US010238349B2

(12) United States Patent
Furuichi et al.

(10) Patent No.: US 10,238,349 B2
(45) Date of Patent: Mar. 26, 2019

(54) IMAGING APPARATUS FOR DIAGNOSIS AND DISPLAY METHOD

(75) Inventors: Junya Furuichi, Isehara (JP); Naoya Iwata, Fujisawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 540 days.

(21) Appl. No.: 13/433,092

(22) Filed: Mar. 28, 2012

(65) Prior Publication Data

US 2012/0253184 A1    Oct. 4, 2012

(30) Foreign Application Priority Data

Mar. 28, 2011    (JP) ................................ 2011-070340

(51) Int. Cl.
*A61B 5/00* (2006.01)
(52) U.S. Cl.
CPC ............ *A61B 5/743* (2013.01); *A61B 5/0066* (2013.01); *A61B 5/7425* (2013.01); *A61B 5/0084* (2013.01); *A61B 5/6876* (2013.01)
(58) Field of Classification Search
USPC ....................................................... 600/425
See application file for complete search history.

(56) References Cited

U.S. PATENT DOCUMENTS

| | | | |
|---|---|---|---|
| 6,187,032 B1 * | 2/2001 | Ohyu et al. ................ | 600/409 |
| 7,621,874 B2 * | 11/2009 | Romley et al. ............ | 600/463 |
| 7,738,941 B2 | 6/2010 | Hirota | |
| 8,025,622 B2 * | 9/2011 | Rold et al. ................ | 600/463 |
| 8,292,816 B2 | 10/2012 | Yoshimura | |
| 2003/0236443 A1 * | 12/2003 | Cespedes ................. | A61B 5/01 600/29 |
| 2006/0013462 A1 * | 1/2006 | Sadikali .................... | 382/132 |
| 2007/0232891 A1 | 10/2007 | Hirota | |
| 2010/0050114 A1 * | 2/2010 | Braun et al. .............. | 715/788 |

(Continued)

FOREIGN PATENT DOCUMENTS

| | | |
|---|---|---|
| EP | 1 839 569 A2 | 10/2007 |
| EP | 2 156 804 A1 | 2/2010 |

(Continued)

OTHER PUBLICATIONS

Extended European Search Report dated Jul. 26, 2012, issued by the European Patent Office in corresponding European Application No. 12160300.5. (11 pages).

*Primary Examiner* — James Kish
(74) *Attorney, Agent, or Firm* — Buchanan Ingersoll & Rooney PC

(57) ABSTRACT

An imaging apparatus for diagnosis comprises a display unit configured to display a longitudinal-sectional image in a first display area, and display a cross-sectional image corresponding to an arbitrary position in an axial direction in the longitudinal-sectional image in a second display area; a signal processing unit divides the second display area into at least two individual areas in case of accepting an instruction to the effect that a predetermined operation is executed with respect to the first display area; and the signal processing unit displays indicators in the first display area, wherein in a case in which the second display area is divided into at least two individual areas, cross-sectional images corresponding to the axial direction position are displayed by at least two indicators in respective individual areas.

14 Claims, 11 Drawing Sheets

(56) References Cited

U.S. PATENT DOCUMENTS

| | | | |
|---|---|---|---|
| 2010/0085273 A1 | 4/2010 | Nakayama | |
| 2010/0131887 A1* | 5/2010 | Salazar-Ferrer et al. | 715/788 |
| 2011/0071404 A1* | 3/2011 | Schmitt et al. | 600/479 |
| 2012/0130242 A1* | 5/2012 | Burgess | A61B 8/12 |
| | | | 600/443 |

FOREIGN PATENT DOCUMENTS

| | | |
|---|---|---|
| JP | 10-262964 A | 10/1998 |
| JP | 2003-325512 A | 11/2003 |
| JP | 2005-334089 A | 12/2005 |
| JP | 2007-267867 A | 10/2007 |
| JP | 2009-240359 A | 10/2009 |
| JP | 2010-014514 A | 1/2010 |

\* cited by examiner

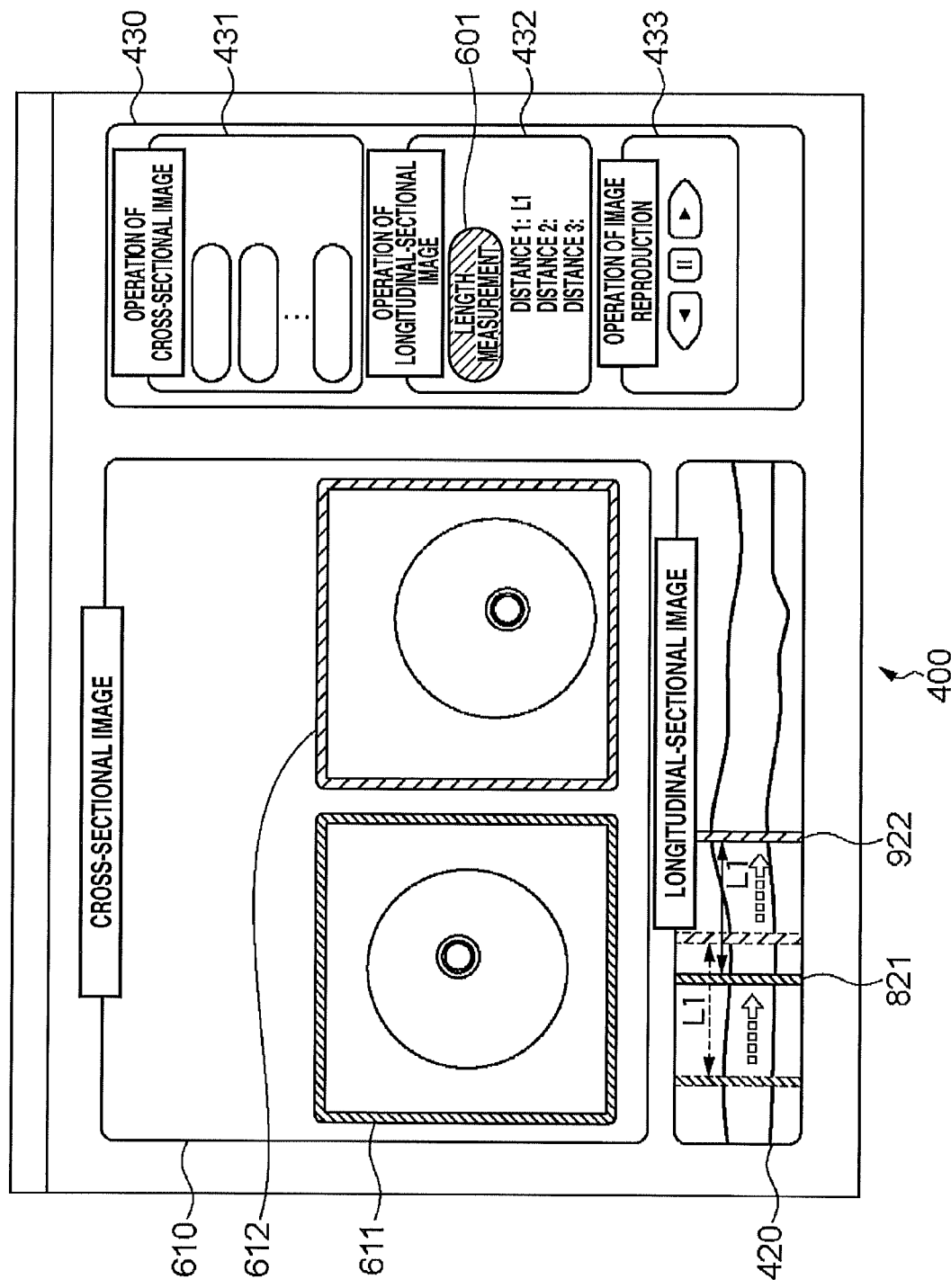

IMAGING APPARATUS FOR DIAGNOSIS AND DISPLAY METHOD

CROSS REFERENCES TO RELATED APPLICATIONS

The present invention contains subject matter related to Japanese Patent Application JP2011-070340 filed in the Japanese Patent Office on Mar. 28, 2011, the entire content of which is incorporated herein by reference.

TECHNICAL FIELD

The present invention generally relates to an imaging apparatus for diagnosis and an image display method.

BACKGROUND DISCUSSION

Ultrasound imaging apparatus used in the past for diagnosis include an optical coherent tomography (OCT) apparatus (see, for example, Japanese Unexamined Patent Publication No. 2010-14514) and also an optical frequency domain imaging (OFDI) apparatus utilizing wavelength sweep, which is an improvement over optical coherent tomography apparatus for diagnosing before operation, at the time of treatment inside a blood vessel depending on a high functional catheter such as a stent and the like, or to conform a result after an operation. Hereinafter, in the present specification, the ultrasound imaging apparatus for diagnosis, the optical coherent tomography (OCT) apparatus and the optical frequency domain imaging (OFDI) apparatus utilizing wavelength sweep will be generically referred to as "imaging apparatus for diagnosis".

For example, in performing diagnosis before an operation, that is before a stent is indwelled, to select and determine the length of the stent to be indwelled, the position at which the stent is indwelled or the like, imaging apparatus for diagnosis are used for measuring the length of the lesion region which becomes the treatment target. Also, to confirm results after the stent is indwelled, imaging apparatus for diagnosis are used to confirm whether or not the indwelled stent covers the desired lesion region.

As a result of the fact that the imaging apparatus for diagnosis has come to be used for such an application, it has been found in recent years that there are many cases in which restenosis after indwelling the stent occurs from the stent edge. Consequently, for example, situations arise in some guidelines in which there is presented a treatment guideline aiming for 50% or less as the plaque ratio at the stent edge on the occasion of the stent indwelling.

Based on such a matter, in the case of the imaging apparatus for diagnosis used in the manner mentioned above, it is desirable to employ a construction which is realized as a constitution in which the situation (sectional image) inside the blood vessel of the portion at which the stent edge is positioned after the indwelling can be relatively easily referred to or understood and also, the length of the stent to be indwelled, the position of the stent to be indwelled or the like can be selected and determined.

In case of a conventional imaging apparatus for diagnosis, it is known to employ an arrangement in which a plurality of cross-sectional images which were imaged continuously in an axial direction are displayed (reproduced) one by one on a display screen in accordance with the imaged order. Consequently, it is easy to grasp the situation inside a blood vessel at a desired position, but it is not necessarily easy for a user to grasp the situation (cross-sectional image) inside the blood vessel at the aforesaid position from the viewpoint of the plaque-ratio confirmation at the portion where the stent edge is positioned after indwelling the stent.

In fact, until now, a user has grasped the situation inside the blood vessel in the portion where the stent edge is positioned by displaying a plurality of cross-sectional images sequentially on the display screen while repeating fast-forwarding/rewinding and suitably changing the position in the axial direction, and so it cannot be said that the work-operation efficiency was excellent. Consequently, in an imaging apparatus for diagnosis, there has been requested an offer of a user interface suitable for the use application.

SUMMARY

The apparatus disclosed here is provides a user interface suitable for a diagnosis before operation, which is applied before indwelling a stent. The imaging apparatus for diagnosis includes a transmitting and receiving unit configured to carry out signal transmission and reception while moving continuously in an axial direction in a living body lumen and to obtain signals reflected from tissue of the living body lumen, a signal processing unit configured to construct a plurality of cross-sectional images in a direction perpendicular to the axial direction of the living body lumen based on the reflected signal, and a display unit. The display unit comprises a first display area configured to display a longitudinal cross—sectional image in an axial direction of the living body lumen constructed using data which is used to construct the respective cross-sectional images, and a second display area configured to display the cross-sectional image corresponding to an arbitrary position in an axial direction in the longitudinal-sectional image displayed in the first display area. The signal processing unit is configured to divide the second display area into at least two individual areas when accepting an instruction that a predetermined operation is executed with respect to the first display area, and display at least two indicators for indicating the position of the axial direction in the longitudinal-sectional image in the first display area in case of accepting the instruction that the predetermined operation is executed. The display unit displays cross-sectional images corresponding to the axial direction position indicated by at least two indicators, in respective individual areas of the second display area, in a case in which the second display area is divided into at least two individual areas.

According to another aspect, an imaging apparatus for diagnosis comprises: a transmitting and receiving unit configured to carry out signal transmission, in which signals are transmitted toward tissue in a living body lumen, and reflected signal reception, in which signals reflected from the tissue in the living body lumen are received, while moving continuously in an axial direction in the living body lumen; a signal processing unit operatively connected to the transmitting and receiving unit and configured to use the reflected signals to generate cross-sectional images of the tissue in a direction perpendicular to the axial direction of the living body lumen; and a display unit. The display unit includes: a first display area configured to display a longitudinal cross-sectional image of the tissue in the living body lumen which has been constructed using data used to generate the cross-sectional images, and to display a first end position indicator on the longitudinal cross-sectional image and a second end position indicator on the longitudinal cross-sectional image that is spaced from the first end position indicator in an axial-direction of the longitudinal cross-sectional image; and a second display area different from the first display area to display the cross-sectional image of the tissue at an axial direction position of the longitudinal cross-sectional image. The signal processing unit is configured to divide the second display area into at least two different individual areas, including one individual area configured to display the cross-sectional image of the tissue at the axial-direction position of the longitudinal cross-sectional image identified by the first end position indicator and an other individual area configured to display the cross-sectional image of the tissue at the axial-direction position of the longitudinal cross-sectional image identified by the second end position indicator.

Another aspect of the disclosure here involves a display method in an imaging apparatus for diagnosis in which a transmitting and receiving unit carrying out signal transmission and reception is moved continuously in an axial direction inside a living body lumen and reflected signals are obtained from tissue in the living body lumen, and a plurality of cross-sectional images in a direction perpendicular to the axial direction of the living body lumen are constructed using the reflected signals. The display method involves: constructing a longitudinal-sectional image in an axial direction of the living body lumen, using data used for constructing the respective cross-sectional images, and displaying the longitudinal-sectional image in a first display area; displaying, in a second display area different from the first display area, the cross-sectional image corresponding to an arbitrary position in an axial direction in the longitudinal-sectional image displayed in the first display area; dividing the second display area into two respective individual areas upon accepting an instruction to execute a predetermined operation with respect to the first display area; displaying, in the first display area, at least two indicators to indicate positions in the axial-direction of the longitudinal-sectional image when accepting the instruction to execute the predetermined operation; and displaying, in the respective individual areas of the second display, the cross-sectional images corresponding to the axial direction positions of the at least two indicators.

BRIEF DESCRIPTION OF THE DRAWINGS

FIG. 11 is a diagram showing one example of a display screen in a display process when operating a longitudinal-sectional image.

DETAILED DESCRIPTION

Set forth below is a detailed description of embodiments of the optical imaging apparatus and display method disclosed here. The illustrated and disclosed embodiments represent examples of the optical imaging apparatus and display method.

First Embodiment

Overall Construction of Imaging Apparatus for Diagnosis

Figure 1:
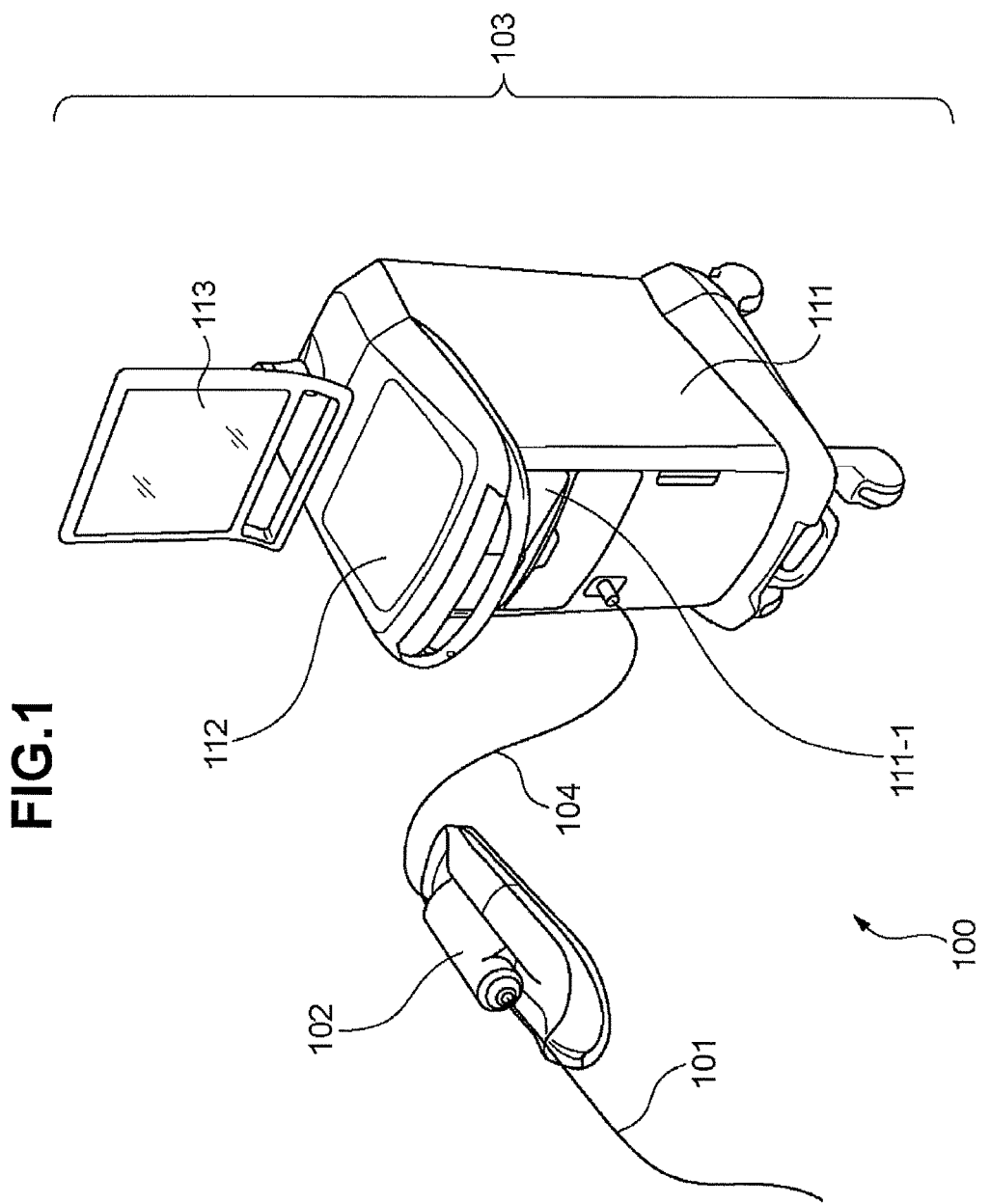
FIG. 1 is a perspective view of the optical imaging apparatus showing the overall outward-appearance of the optical imaging apparatus for diagnosis according to one embodiment disclosed by way of example.

Referring initially to FIG. 1, the description which follows describes an imaging apparatus for diagnosis according to one embodiment disclosed by way of example. As mentioned above, the imaging apparatus for diagnosis includes an ultrasound imaging apparatus for diagnosis, an optical coherent tomography (OCT) apparatus and an optical frequency domain imaging (OFDI) apparatus utilizing wavelength sweep. The following description of the overall construction (outward-appearance construction) will be explained with respect to the optical coherent tomography (OCT) apparatus and the optical frequency domain imaging (OFDI) apparatus utilizing wavelength sweep which constitute optical imaging apparatuses for diagnosis.

FIG. 1 illustrates the outward-appearance construction or overall construction of an optical imaging apparatus for diagnosis (optical coherent tomography apparatus or optical frequency domain imaging apparatus utilizing wavelength sweep) 100.

As shown in FIG. 1, the optical imaging apparatus for diagnosis 100 is provided with an optical probe unit 101, a scanner & pull-back unit 102 and an operation control apparatus 103/. The scanner & pull-back unit 102 and the operation control apparatus 103 are connected by a signal line 104.

The optical probe unit 101 is inserted directly inside a lumen or tubular tissue of a blood vessel or the like and transmits the transmitted measurement light continuously toward the tissue and concurrently, is inserted with an imaging core provided at the distal end with a transmission and receiving unit for receiving the reflected light from the tissue continuously, and the state or condition of the tissue is measured or determined by using the imaging core.

The scanner & pull-back unit 102 is constructed such that the optical probe unit 101 is detachably attached or connected to the scanner & pull-back unit 102 and realizes a radial operation and pull-back operation (operation in the rotational direction and operation in the axial direction inside the lumen) of the imaging core inserted in the optical probe unit 101 depending on the driving operation of an installed motor. Also, a reflected light received by the transmitting and receiving unit is obtained and concurrently, the obtained reflected light is transmitted to the operation control apparatus 103 through the signal line 104.

The operation control apparatus 103, on an occasion when carrying out measurement, functions to input various kinds of set values, and also functions to display the measurement result as a cross-sectional image of the tubular tissue. The operation control apparatus 103 thus serves as an input means for inputting information and display means for displaying the measurement result.

The operation control apparatus 103 includes a main body control unit 111, and interference signal data are generated by making the reflected light obtained by the measurement and the reference light obtained by separating the measurement light interfere with each other and concurrently, multiple cross-sectional images in a direction perpendicular to the axis of the lumen or tissue is constructed by processing line data generated based on the interference signal data. The line data is defined as data array which makes a line from the center of the cross-sectional image to the edge of the cross-sectional image. The line date is produced from coherent light intensity of the emission direction of the transmitting.

The reference numeral 111-1 indicates a printer & DVD recorder. The processed result in the main body control unit 111 is printed and is stored as data signals. The reference numeral 112 indicates an operation panel at which a user can input various kinds of set values and various kinds of instructions through the operation panel 112. The reference numeral 113 indicates an LCD monitor as a display apparatus, i.e., display unit, and it displays a plurality of cross-sectional images of the tubular tissue, which are constructed in the main body control unit 111.

Operational or Functional Construction of Imaging Apparatus for Diagnosis

The description which follows will next explain the operational or functional construction of the imaging apparatus for diagnosis 100. As mentioned above, there are included, in the optical imaging apparatus for diagnosis within the imaging apparatus for diagnosis, further an optical coherent tomography apparatus (OCT) and an optical frequency domain imaging (OFDI) apparatus utilizing wavelength sweep. But the description which follows will mainly be with reference to an optical frequency domain imaging (OFDI) apparatus utilizing wavelength sweep.

Figure 2:
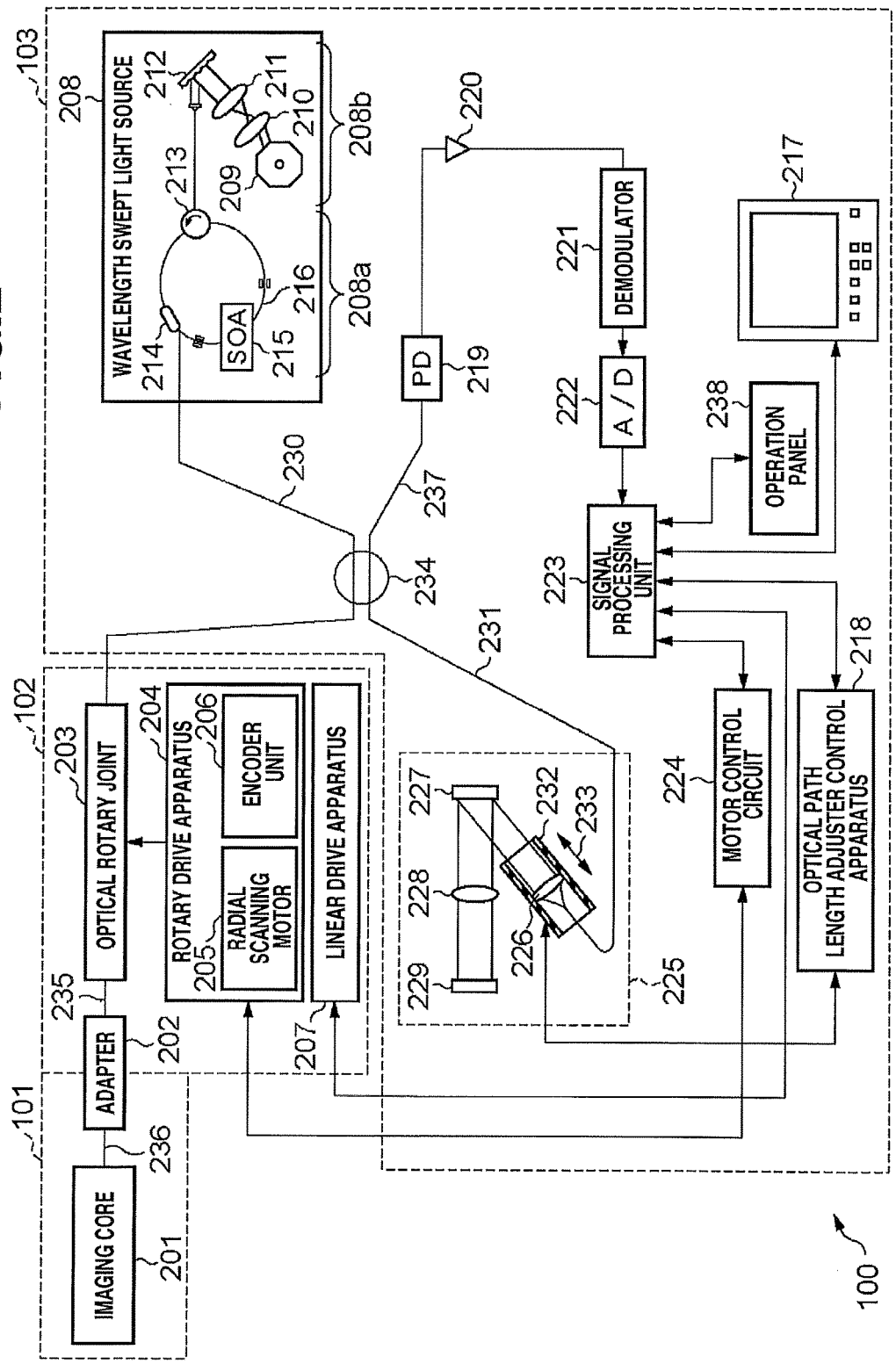
FIG. 2 is a schematic diagram showing features and functional aspects of the imaging apparatus for diagnosis.

FIG. 2 schematically illustrates the optical coherent tomography apparatus utilizing wavelength sweep, which is an imaging apparatus for diagnosis 100.

The reference numeral 208 indicates a wavelength-swept light source. In the illustrated embodiment, a Swept Laser is used. The wavelength-swept light source 208 using the Swept Laser is one kind of an Extended-cavity Laser which is composed of an optical fiber 216 connected with SOA215 (semiconductor optical amplifier) having a ring or annular shape and a polygon scanning filter (208b).

The light outputted from the SOA215 proceeds inside the optical fiber 216 and enters the polygon scanning filter 208b and the light of wavelength selected here is amplified by the SOA215 and finally, it is outputted from a coupler 214.

In the polygon scanning filter 208b, the wavelength is selected depending on the combination of a diffraction grating 212 for light-splitting the light and a polygon mirror 209. Specifically, the light which is light-split by the diffraction grating 212 is focused on the surface of the polygon mirror 209 depending on two pieces of lenses (210, 211). Thus, only the light of the wavelength perpendicular to the polygon mirror 209 returns to the same optical path and is outputted from the polygon scanning filter 208b. Consequently, it is possible to carry out the time sweep of the wavelength by rotating the polygon mirror 209.

For the polygon mirror 209, for example, a 72-facets mirror is used and the rotation speed thereof is around 50000 rpm. Owing to the wavelength sweep system in which the polygon mirror 209 and the diffraction grating 212 are combined, it is possible to employ the wavelength sweep of high speed and high power.

The light of the wavelength swept light source 208, which is outputted from a coupler 214, enters one end of a first single mode fiber 230 and is transmitted to the distal end side. The first single mode fiber 230 is optically connected, along the way, with a second single mode fiber 237 and a third single mode fiber 231 in a photo coupler unit 234. Therefore, the light made to enter the first single mode fiber 230 is transmitted by being split into three optical paths at the maximum by this photo coupler unit 234.

On the distal end side from the photo coupler unit 234 of the first single mode fiber 230, there is provided, in a rotary drive apparatus 204, an optical rotary joint 203 which connects between a non-rotary portion and a rotary portion and which transmits the light.

Further, on the distal end side of a fourth single mode fiber 235 in the inside of the optical rotary joint 203, there is connected, freely detachably through an adapter 202, a fifth single mode fiber 236 of the optical probe unit 101. Consequently, the light from the wavelength swept light source 208 is transmitted to the fifth single mode fiber 236 which passes-through an imaging core 201 and which is rotary-drivable.

The transmitted light is illuminated from a distal end side of the imaging core 201 with respect to the tissue while being radially operated. Then, a portion of the reflected light which is scattered on the surface of or in the inside of the lumen or tissue (for example, blood vessel) is taken-in by the imaging core 201 and returns to the first single mode fiber 230 side through the reverse optical path. Further, the light is light-received by a photo detector (for example, photo diode 219) owing to a fact that a portion thereof moves to the second single mode fiber 237 side by the photo coupler unit 234 and is emitted from one end of the second single mode fiber 237.

It should be noted that the rotary portion side of the optical rotary joint 203 is rotationally driven by a radial scanning motor 205 of the rotary drive apparatus 204. Also, the rotary angle of the radial scanning motor 205 is detected by an encoder unit 206. Further, the scanner & pull-back unit 102 is provided with a linear drive apparatus 207 and defines the axial-direction operation of the imaging core 201 based on an instruction from a signal processing unit 223.

On the other hand, there is provided a variable mechanism 225 of the optical path length for fine-adjusting the optical path length of the reference light at a distal end on the opposite side with respect to the photo coupler unit 234 of the third single mode fiber 231.

The variable mechanism 225 of this optical path length functions as an optical path length changing unit for changing the optical path length which corresponds to the fluctuation of the length thereof such that the fluctuation or variation in the length of the individual optical probe unit 101 can be absorbed in case of exchanging the optical probe unit 101 for a different one.

Specifically, the third single mode fiber 231 and a collimating lens 226 are provided on a one-axis stage 232 which is freely movable in the optical axis direction thereof as shown by an arrow 233.

Then, in case of exchanging the optical probe unit 101, the one-axis stage 232 realizes a function as the optical path length changing unit by moving in such an amount of variable range of the optical path length, which can absorb the fluctuation of the optical path length of the optical probe unit 101. The one-axis stage 232 functions also as an adjuster for adjusting an offset. For example, in a case in which the distal end of the optical probe unit 101 is not closely-attached to the surface of the biological tissue, it becomes possible, by minutely changing the optical path length by the one-axis stage, to set it to a state of interfering with the reflected light from the surface position of the biological tissue.

The light whose optical path length is fine-adjusted by the variable mechanism 225 of the optical path length is mixed with the light obtained from the first single mode fiber 230 side by the photo coupler unit 234 which is provided on the way of the third single mode fiber 231 and it is light-received by the photo diode 219 through the second single mode fiber 237.

The interfered light which is light-received by the photo diode 219 in this manner is photoelectrically converted and amplified by an amplifier 220 and, thereafter, is inputted to a demodulator 221. In this demodulator 221, a demodulation process for extracting only the signal component of the interfered light is carried out and the output thereof is inputted to an A/D converter 222 as the interference signal.

In the A/D converter 222, the interference signal is subjected to sampling, for example, at 180 MHz for 2048 points and digital data (interference signal data) of one line are generated. The reason the sampling frequency is set at 180 MHz in this disclosed example is due to an assumption that about 90% of the period of wavelength sweep (12.5 μsec) can be extracted as digital data of 2048 points in case of setting the repetition frequency of wavelength sweep at 80 kHz, though the apparatus and method are not limited by this aspect in particular.

The interference signal data of one line unit, generated in the A/D converter 222, are inputted to the signal processing unit 223. In the signal processing unit 223, the interference signal data are frequency-decomposed by FFT (Fast Fourier Transform) and then, there are generated data in the depth direction (line data), and by coordinate-converting those data, there is constructed a cross-sectional image at each position in the axial direction inside the lumen (blood vessel) and it is outputted, under an instruction from the operation panel 238 (corresponding to reference numeral 112 of FIG. 1), to an LCD monitor 217 (corresponding to reference numeral 113 of FIG. 1) at a predetermined frame rate.

The signal processing unit 223 is connected further with an optical path length adjuster control apparatus 218. The signal processing unit 223 carries out control of the position of the one-axis stage 232 by means of the optical path length adjuster control apparatus 218. Also, the signal processing unit 223 is connected with a motor control circuit 224 and receives a video synchronization signal from the motor control circuit 224. In the signal processing unit 223, the construction of the cross-sectional images is carried out in synchronization with the received video synchronization signal.

In addition, the video synchronization signal of this motor control circuit 224 is transmitted also to the rotary drive apparatus 204 and in the rotary drive apparatus 204, a drive signal in synchronization with the video synchronization signal is outputted.

Operational Construction of Signal Processing Unit

The description which follows explains the operational or functional construction for realizing various kinds of processes in the signal processing unit 223 of the imaging apparatus for diagnosis 100. Within various kinds of processes realized in the signal processing unit 223, the following description is presented centering around a process of constructing a cross-sectional image in the direction perpendicular to the axis and a process of constructing a longitudinal-sectional image in the axial direction (construction process), and also centering around a process of storing line data inside the signal processing unit 223 (storage process).

It is possible for the image construction process and the storage process, which will be explained hereinafter, to be realized by using dedicated hardware and also, for the function of each unit to be realized by software (by a configuration in which a computer executes computer-readable non-transitory programs).

Figure 3:
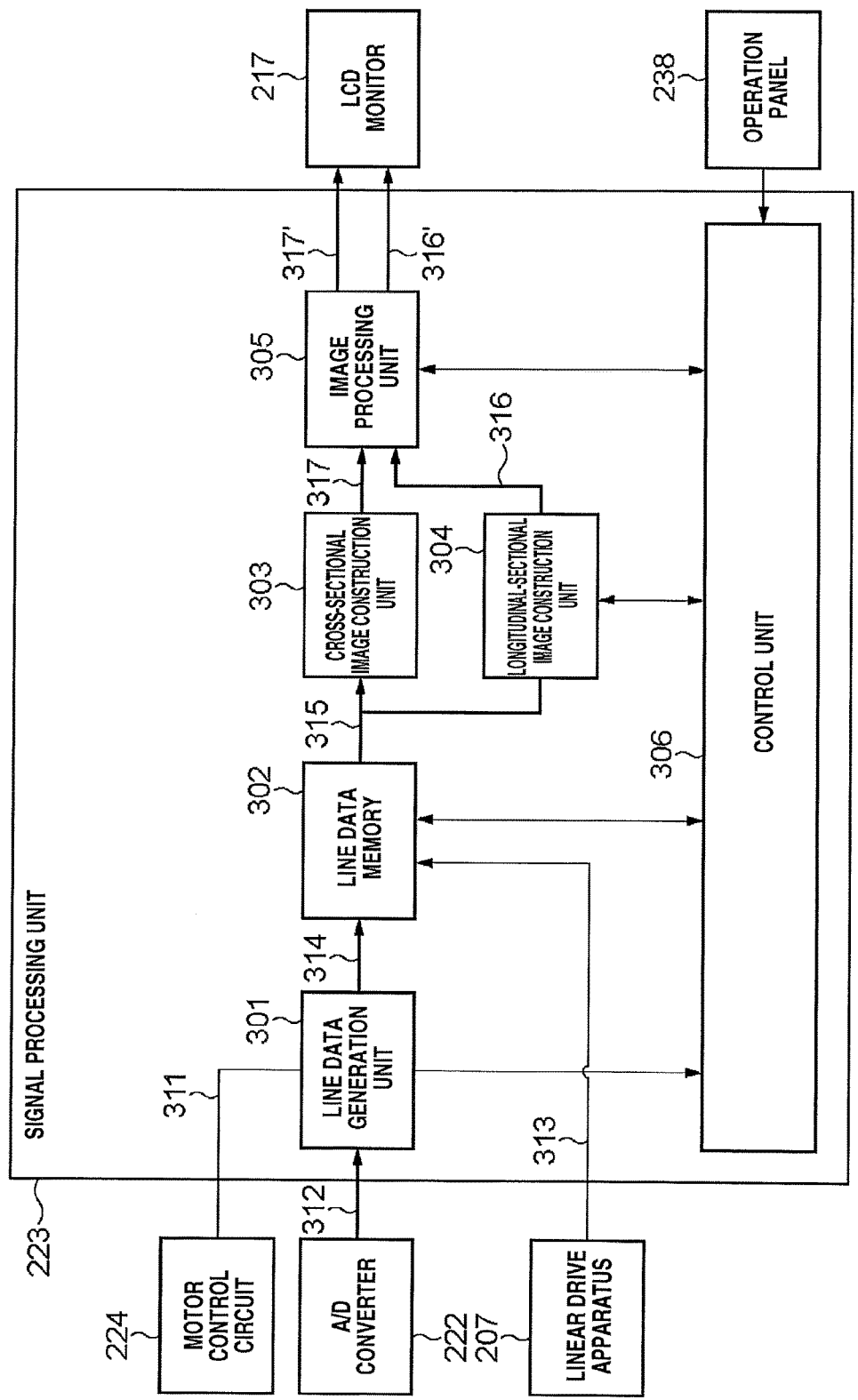
FIG. 3 is a diagram showing features and functional aspects of a signal processing unit.

FIG. 3 is a diagram illustrating aspects of the apparatus for realizing the image construction process and the storage process in the signal processing unit 223 of the imaging apparatus for diagnosis 100, and showing a functional block other than the signal processing unit 223 associated with the aforesaid processes.

As shown in FIG. 3, the interference signal data generated in the A/D converter 222 is processed in a line data generation unit 301 inside the signal processing portion 223 or forming a part of the signal processing unit such that the number of lines per rotation of the radial scanning motor becomes 512 by using a signal of the encoder unit 206 of the radial scanning motor 205, which is outputted from the motor control circuit 224.

The embodiment disclosed here by way of example is such that the cross-sectional image is composed of 512 lines, but the number of lines is not limited by this number.

The line data 314 outputted from the line data generation unit 301 is stored in the line data memory 302 for every one rotation of the radial scanning motor based on an instruction from the control unit 306. At that time, in the control unit 306, a pulse signal 313 outputted from a moving amount detector of the linear drive apparatus 207 is counted beforehand and thereafter, when storing the line data 314 into the line data memory 302, the storing is carried out by being correlated with count values counted upon generation of the respective line data 314.

Note that a case was explained here in which the line data memory 302 is arranged and the line data 314 is stored by correlating it with the count value of the pulse signal 313 outputted from the moving amount detector of the linear drive apparatus 207, but the apparatus and method disclosed here are not limited in this regard. For example, a constitution is possible in which a cross-sectional image data memory is arranged following the cross-sectional image construction unit 303 and the cross-sectional image 317 is stored in such a manner as to be correlated with the count value of the pulse signal 313 outputted from the moving amount detector of the linear drive apparatus 207.

Returning to the arrangement shown in FIG. 3, based on the instruction from the control unit 306, the line data 315 stored by being correlated with the count value is subjected to various kinds of processes (line addition-averaging process, filtering process and the like) in the cross-sectional image construction unit 303 and thereafter, is sequentially outputted as a cross-sectional image 317 by being subjected to Polar to Rectangular Conversion.

Further, in the image processing unit 305, image processing for displaying on the LCD monitor 217 is applied and thereafter, it is outputted to the LCD monitor 217 as a cross-sectional image 317' in the direction perpendicular to the axis.

Also, the line data 315 stored by being correlated with the count value is read out by the longitudinal-sectional image construction unit 304 based on the instruction from the control unit 306. In the longitudinal-sectional image construction unit 304, a longitudinal-sectional image 316 in the axial direction is constructed by using the read out line data 315.

Here, as an example, an example was explained in which the longitudinal-sectional image 316 is constructed from the line data 315, but the apparatus and method disclosed here are not limited in this regard, and a constitution can be employed such that the longitudinal-sectional image is constructed from the cross-sectional image 317.

The constructed longitudinal-sectional image 316 is read out by the image processing unit 305 based on the instruction from the control unit 306, is subjected to image processing so as to be displayed on the LCD monitor 217, and then is outputted to the LCD monitor 217 as a longitudinal-sectional image 316'.

In the LCD monitor 217, the cross-sectional image 317' processed in the image processing unit 305 and the longitudinal-sectional image 316' are displayed in parallel. Also, the cross-sectional image 317' constructed by using respective line data inside the line data memory 302, correlated with the same count value as that of the line data aligned at the position corresponding to the instruction inputted from the user through the operation panel 238, is redisplayed.

The following description will explain in detail the display of the cross-sectional image 317' and the longitudinal-sectional image 316' on the LCD monitor 217, and the redisplay of the cross-sectional image 317' corresponding to the instruction inputted by the user through the operation panel 238.

Display Screen Displayed on LCD Monitor of Imaging Apparatus for Diagnosis

Figure 4:
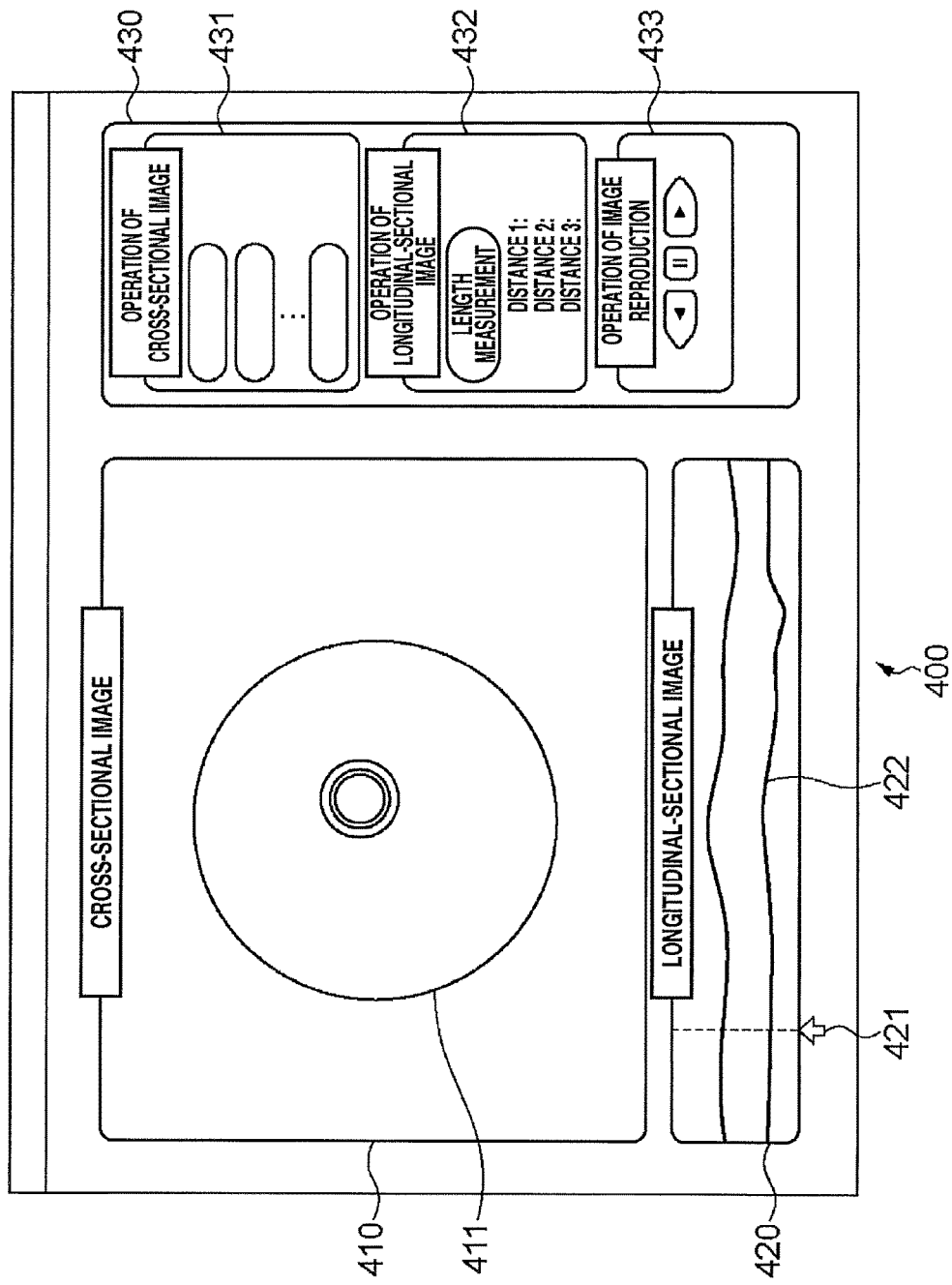
FIG. 4 is a diagram showing one example of a display screen displayed on a monitor of the imaging apparatus for diagnosis.

First, it is explained with respect to a display screen displayed on the LCD monitor 217 of the imaging apparatus for diagnosis 100. FIG. 4 is a diagram showing one example of a display screen 400 for displaying the cross-sectional image 317' and the longitudinal-sectional image 316' on the LCD monitor 217 of the imaging apparatus for diagnosis 100.

As shown in FIG. 4, the display screen 400 is provided with a cross-sectional image display area 410 which displays the cross-sectional image sequentially, a longitudinal-sectional image display area 420 which displays a longitudinal-sectional image, and an operation area 430 for carrying out various kinds of operations with respect to the aforesaid areas 410, 420.

The operation area 430 is further provided with a cross-sectional image operation area 431 which carries out the operation with respect to the cross-sectional image displayed on the cross-sectional image display area 410, a longitudinal-sectional image operation area 432 which carries out the operation with respect to the longitudinal-sectional image displayed on the longitudinal-sectional image display area 420 and an image reproduction operation area 433 which carries out the operation for reproducing the cross-sectional images along the axial direction on the cross-sectional image display area 410.

Based on the arrangement discussed above, a predetermined file is read out, and by operating various kinds of buttons of the image reproduction operation area 433, it is possible to continuously display a plurality of cross-sectional images in the cross-sectional image display area 410, to temporarily stop the displaying of a plurality of cross-sectional images which are being sequentially displayed, and further, to sequentially display the plurality of cross-sectional images by fast-forwarding or rewinding them. In the example of FIG. 4, there is shown an aspect in which a cross-sectional image 411 corresponding to the predetermined position in the axial direction (position indicated by an arrow 421 with respect to a longitudinal-sectional image 422 of the longitudinal-sectional image display area 420) is displayed.

In the state shown in FIG. 4, by operating various kinds of buttons of the operation area 430, it is possible to designate predetermined areas of the cross-sectional image 411 and the longitudinal-sectional image 422, and to calculate the areas and various lengths of the designated predetermined areas. The description below will explain a display process in case of operating various kinds of buttons of the longitudinal-sectional image operation area 432 in particular.

Display Screen in Display Process when Operating Longitudinal-Sectional Image

The following description explains, with reference to FIGS. 5-9, the display process in the case of operating the longitudinal-sectional image operation area 432.

Figure 5:
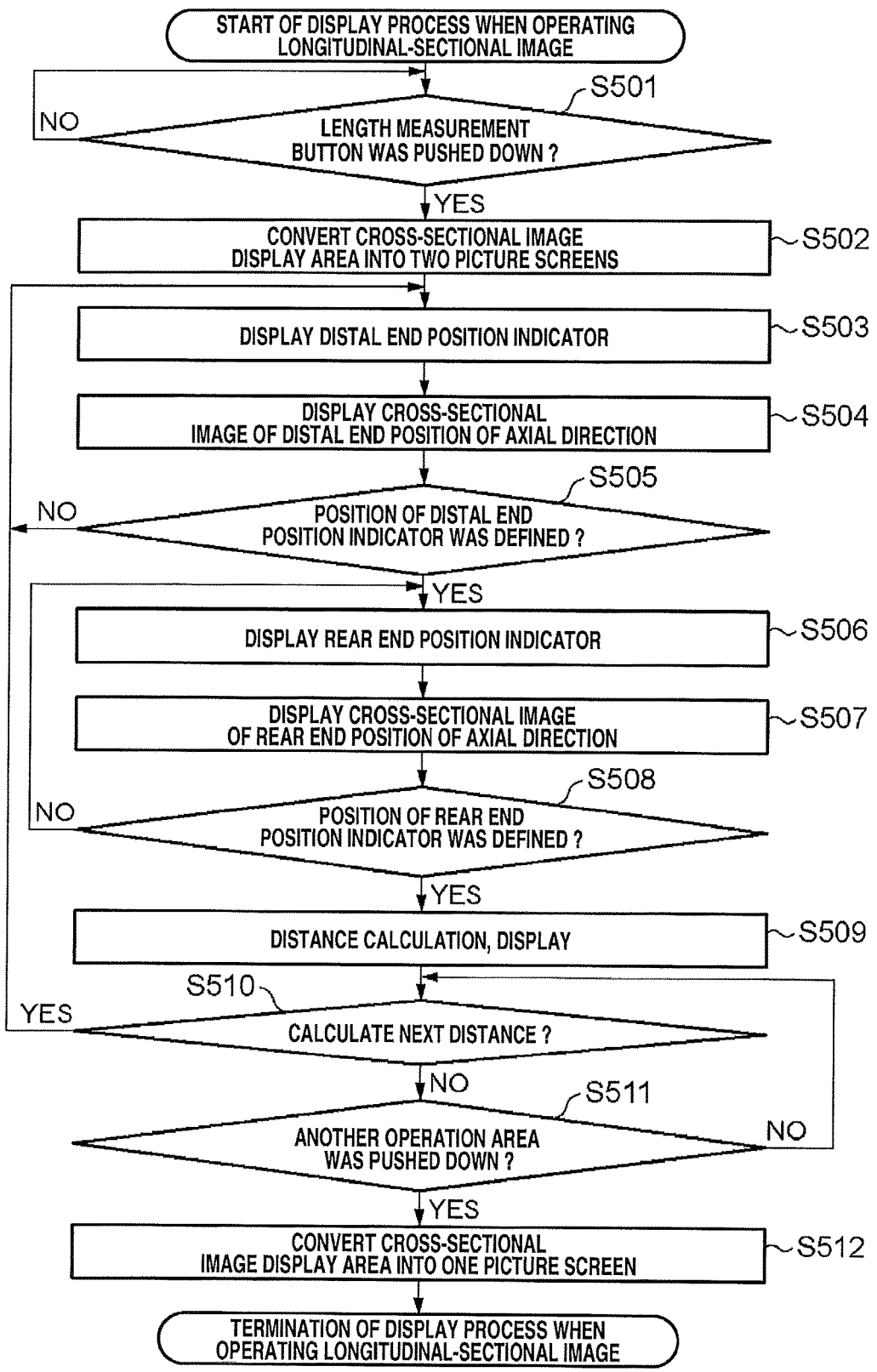
FIG. 5 is a flowchart showing operational aspects of a display process when operating a longitudinal-sectional image.

FIG. 5 is a flowchart showing a flow of the display process when operating the longitudinal-sectional image, and FIG. 6 to FIG. 9 are diagrams showing the display screen 400 in respective processes of the display process when operating the longitudinal-sectional image. The description hereinafter will explain a flow of the display process at the time of operation of the longitudinal-sectional image shown in FIG. 5 while referring to FIG. 6 to FIG. 9.

In step S501, it is judged whether or not the length measurement button 601 of the longitudinal-sectional image operation area 432 has been pushed down (has been operated). In a case in which it is judged that the length measurement button 601 has not been pushed down (has not been operated) in step S501, waiting takes place until it is pushed down (has been operated).

Figure 6:
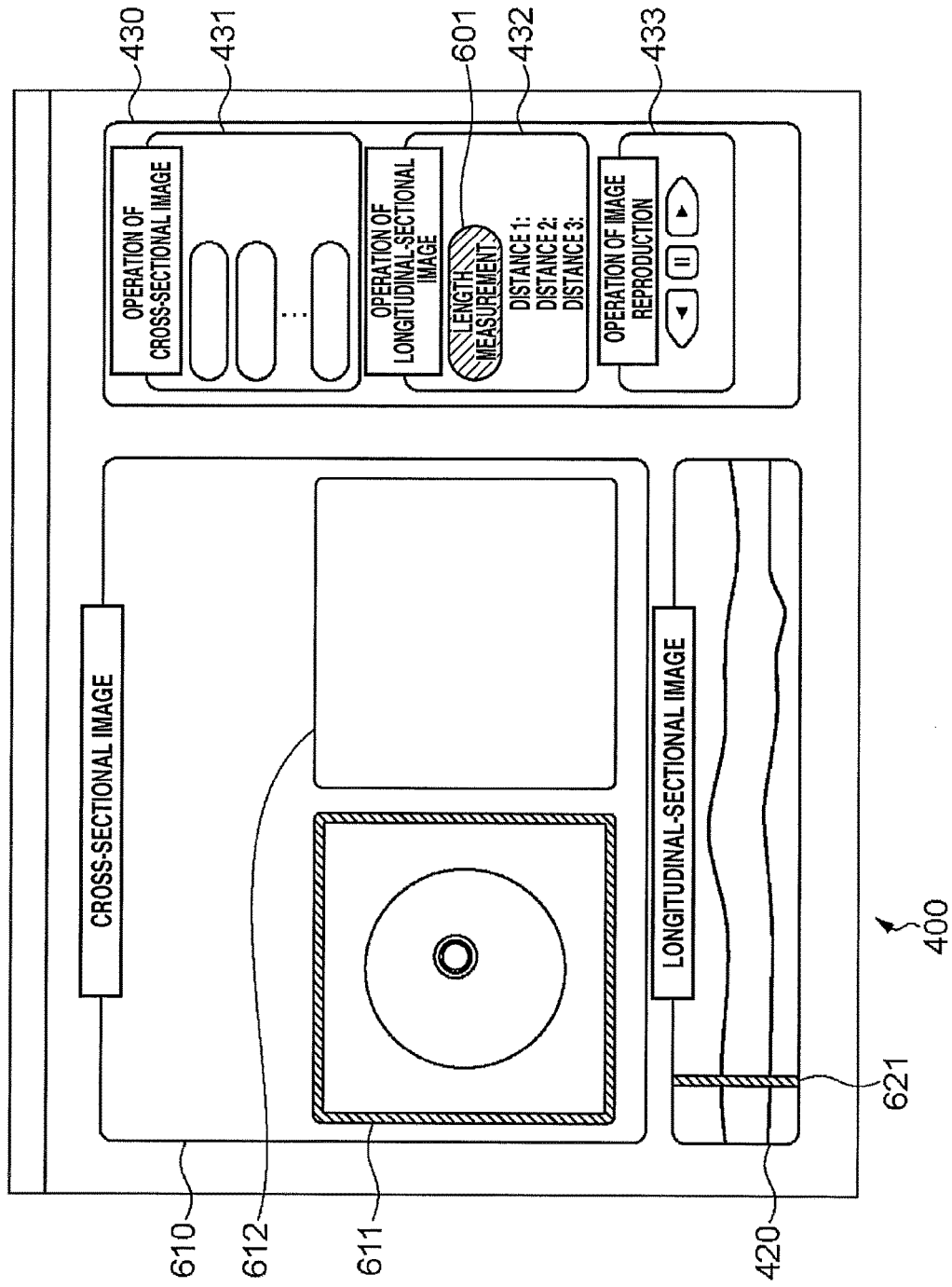
FIG. 6 is a diagram showing one example of a display screen in a display process when operating a longitudinal-sectional image.

On the other hand, in a case in which it is judged that the length measurement button 601 has been pushed down (has been operated) in step S501, the process proceeds to step S502 and the cross-sectional image display area 410 is divided into two picture screens. FIG. 6 shows the cross-sectional image display area 610 divided into the two picture screens in step S502.

As shown in FIG. 6, the cross-sectional image display area 610 is divided into two rectangular areas 611, 612 of equal size. At that time, the cross-sectional image displayed on the cross-sectional image display area 410 immediately before the division is displayed in a demagnified manner on the rectangular area 611, and there is nothing displayed on the rectangular area 612.

In step S503, the distal end position indicator is displayed on the longitudinal-sectional image display area 420. The distal end position indicator is an indicator by which the cross-sectional image at the position in the axial-direction serving as a candidate for the distal end position of the stent is displayed on the cross-sectional image display area 610 in order to decide the distal end position when indwelling the stent. FIG. 6 shows an aspect in which the distal end position indicator 621 is displayed on the longitudinal-sectional image display area 420. The distal end position indicator 621 displayed on the longitudinal-sectional image display area 420 is constituted so as to be movable in the axial direction within the longitudinal-sectional image display area 420.

In step S504, the cross-sectional image corresponding to the position indicated by the distal end position indicator 621 is displayed on the rectangular area 611.

In step S505, it is judged whether or not the position of the distal end position indicator 621 has been determined or set. In step S505, in a case in which it is judged that the position of the distal end position indicator 621 has not been determined, the process returns to step 503 and waits, while updating the distal end position indicator 621 and the cross-sectional image, until it is judged that the position has been determined. In this state, the cross-sectional image displayed on the rectangular area 611 changes every time the distal end position indicator 621 is moved in the axial direction within the longitudinal-sectional image display area 420.

In step S505, when it is judged that the position of the distal end position indicator 621 has been determined or set, the process proceeds to step S506 and the rear end position indicator is displayed on the longitudinal-sectional image display area 420. The rear end position indicator is an indicator by which the cross-sectional image of the position of the axial-direction, which becomes a candidate for the rear end position of the stent, is displayed on the cross-sectional image display area 610 in order to decide the rear end position when indwelling the stent and concurrently, by which the distance with respect to the distal end position indicator 621 is calculated in order to decide the length of the stent to be indwelled.

Figure 7:
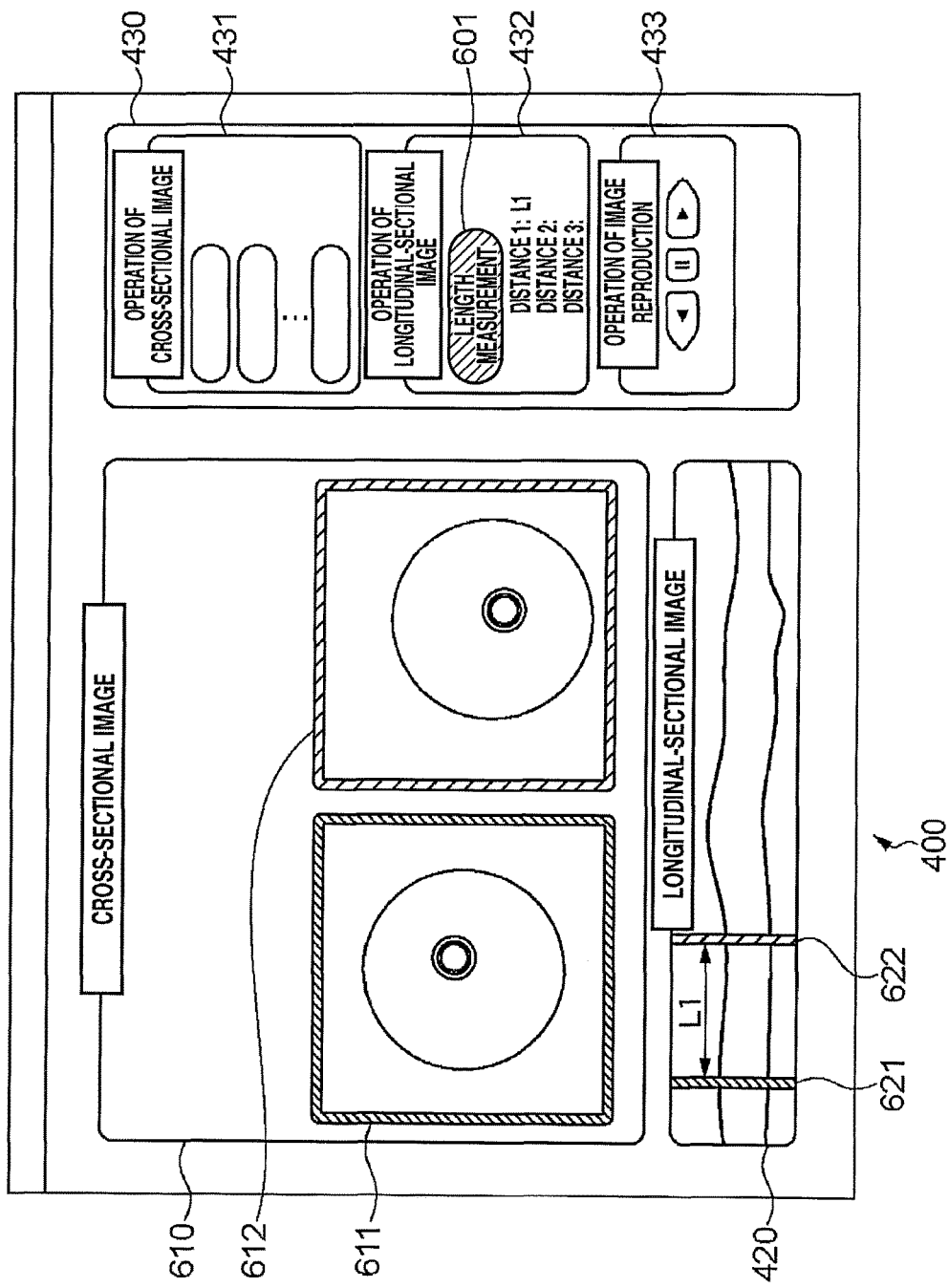
FIG. 7 is a diagram showing one example of a display screen in a display process when operating a longitudinal-sectional image.

In step S507, the cross-sectional image corresponding to the position indicated by the rear end position indicator is displayed on the rectangular area 612. FIG. 7 shows an aspect in which the rear end position indicator 622 is displayed on the longitudinal-sectional image display area 420 and concurrently, the cross-sectional image corresponding to the position indicated by the rear end position indicator 622 is displayed on the rectangular area 612. The rear end position indicator 622 displayed inside the longitudinal-sectional image display area 420 is constituted so as to be movable in the axial direction within the longitudinal-sectional image display area 420.

In step S508, it is judged whether or not the position of the rear end position indicator 622 has been determined or set. In step S508, in a case in which it is judged that the position of the rear end position indicator 622 has not been determined, the process returns to step 506 and waits until it is judged that the position has been determined. In this state, the cross-sectional image displayed on the rectangular area 612 changes every time when the rear end position indicator 622 is moved in the axial direction within the longitudinal-sectional image display area 420. The cross-sectional image changes to reflect the cross-sectional image at the location of the rear end position indicator 622.

In step S508, in a case in which it is judged that the position of the rear end position indicator 622 has been determined or set, the process proceeds to step S509.

In step S509, the distance between the distal end position indicator 621 and the rear end position indicator 622 is calculated, and the calculated result is displayed on the longitudinal-sectional image display area 420 and the longitudinal-sectional image operation area 432. FIG. 7 shows an aspect in which the position of the rear end position indicator 622 is determined and the distance (L1) between the distal end position indicator 621 and the rear end position indicator 622, and distance display line, are displayed on the longitudinal-sectional image display area 420 and the longitudinal-sectional image operation area 432.

In this manner, by employing an arrangement in which the cross-sectional images corresponding to the distal end position indicator 621 and the rear end position indicator 622 respectively are displayed on the rectangular areas 611, 612 simultaneously, it becomes possible for a user to visually confirm the cross-sectional images of the distal end position candidate and the rear end position candidate of the stent simultaneously when indwelling the stent. Further, in a case in which the positions of the distal end position indicator 621 and the rear end position indicator 622 are determined, employing a constitution in which the distance between them is calculated and displayed makes it possible for a user to recognize or know the distance between the distal end position candidate and the rear end position candidate. Thus, it becomes possible to relatively easily select and determine the position and the length of the stent to be indwelled.

Referring once again to FIG. 5, in step S510, a user makes a judgment about whether or not to take another distal end position candidate and another rear end position candidate into account. Specifically, it is judged whether or not the length measurement button 601 of the longitudinal-sectional image operation area 432 has been pushed down (has been operated) again, and in a case in which it is judged that it has been pushed down (has been operated) again, it is newly judged that there is an intention of taking another distal end position candidate and another rear end position candidate into account, and the process returns to step S503.

Figure 8:
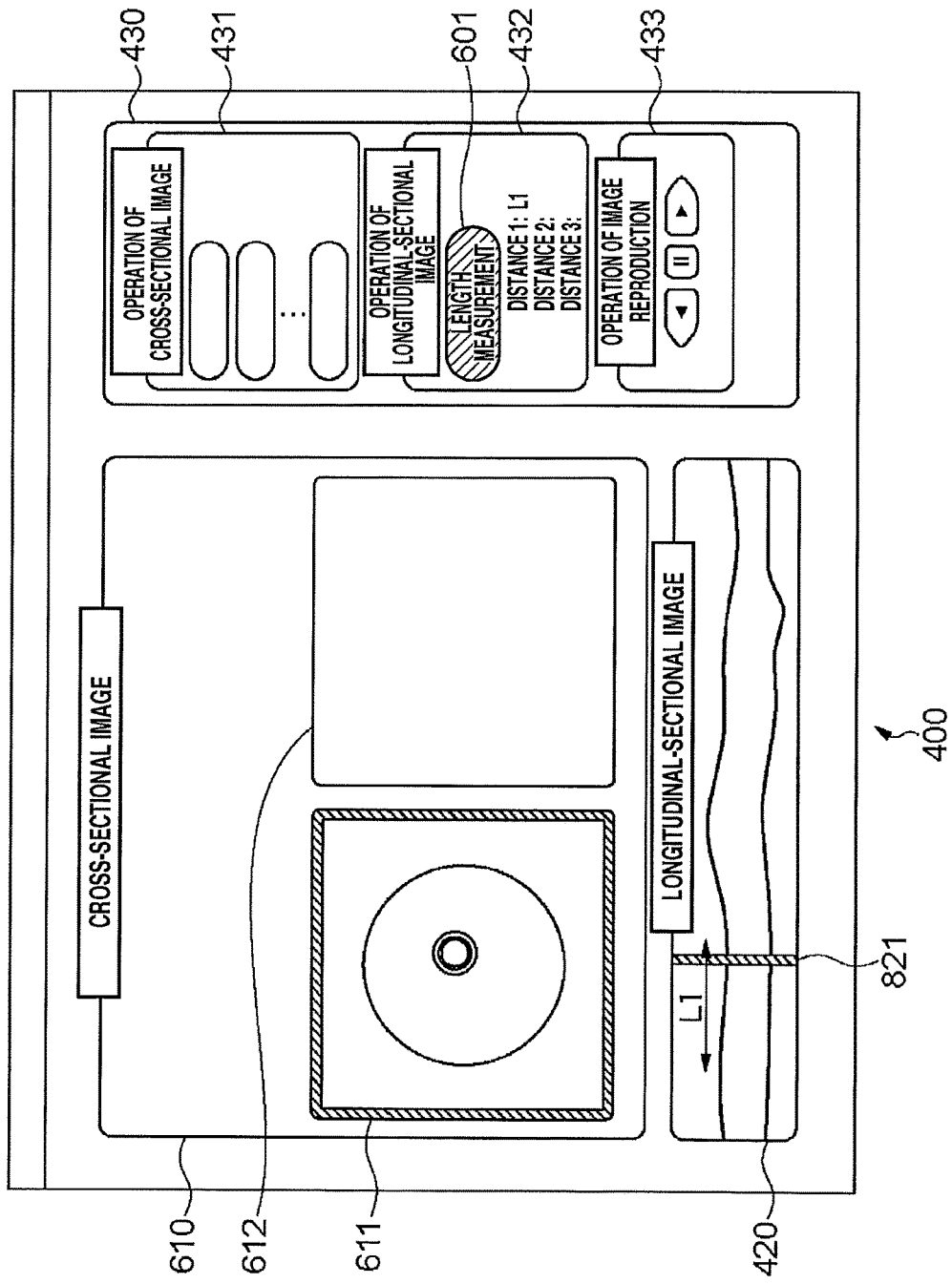
FIG. 8 is a diagram showing one example of a display screen in a display process when operating a longitudinal-sectional image.

In step S503, the distal end position indicator 621 and the rear end position indicator 622 which are displayed on the longitudinal-sectional image display area 420 are deleted and newly, the distal end position indicator is displayed. FIG. 8 is a diagram showing an aspect in which it is judged that a user has an intention of taking another distal end position candidate and another rear end position candidate into account in step S510 and, a distal end position indicator 821 is displayed newly in step S503.

As shown in FIG. 8, the distal end position indicator 821 is newly displayed on the longitudinal-sectional image display area 420. Note that the distance between the distal end position indicator 621 and the rear end position indicator 622 calculated when the length measurement button 601 is pushed down for a first time is displayed continuously as it is.

Hereinafter, in step S504 to step S508, there are executed the same processes as the processes when the length measurement button 601 is pushed down for a first time. In step S509, after the length measurement button 601 is pushed down for a second time, the distance between the determined distal end position indicator and the rear end position indicator is calculated, and the calculated result is displayed on the longitudinal-sectional image display area 420 and the longitudinal-sectional image operation area 432.

Figure 9:
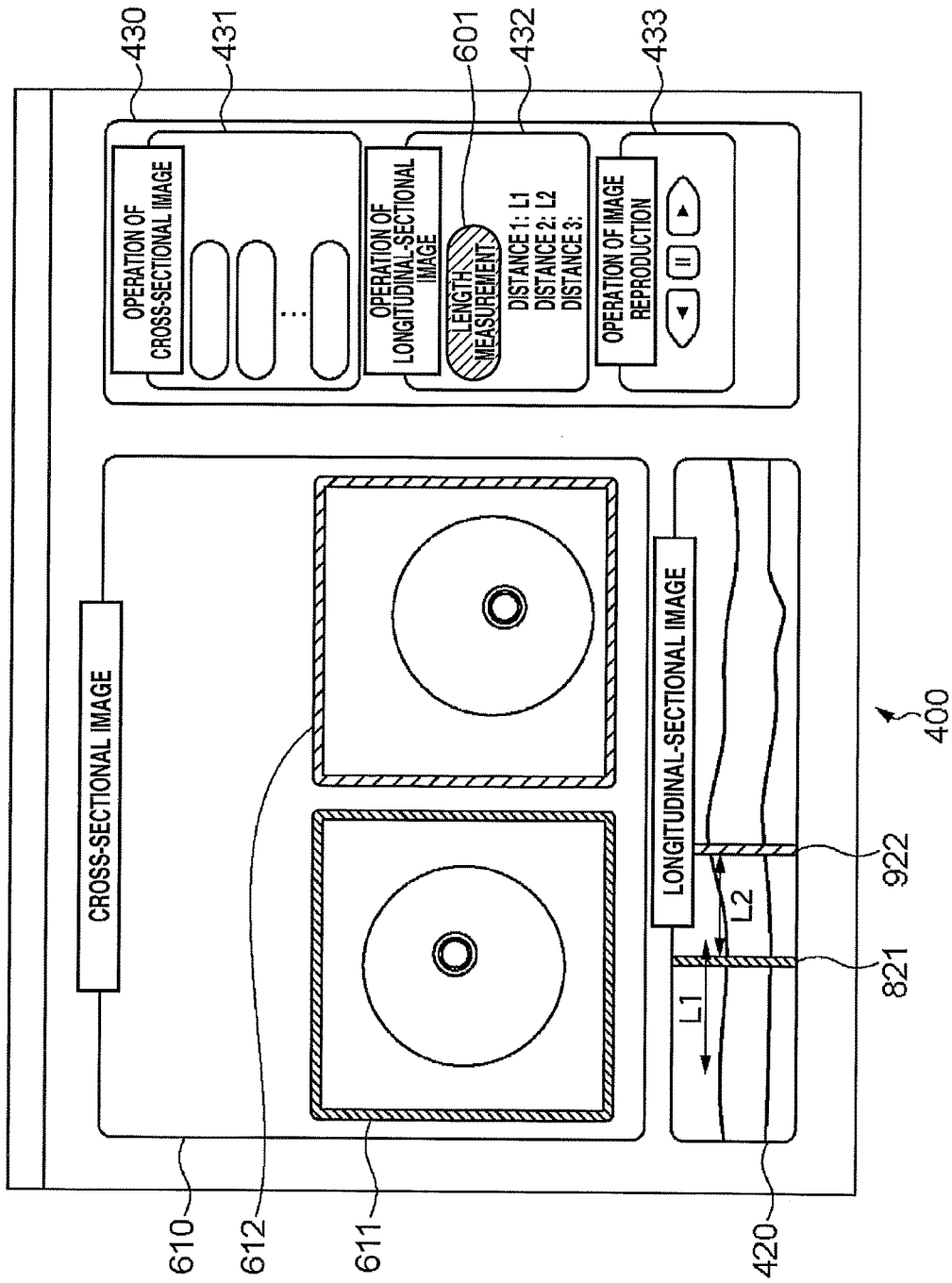
FIG. 9 is a diagram showing one example of a display screen in a display process when operating a longitudinal-sectional image.

FIG. 9 shows an aspect in which the positions of the distal end position indicator 821 and the rear end position indicator 922 are determined, and the distance (L2) and the distance display line between the distal end position indicator 821 and the rear end position indicator 922 are displayed on the longitudinal-sectional image display area 420 and the longitudinal-sectional image operation area 432.

On the other hand, in step S510, in a case in which it is judged that a user has no intention of taking another distal end position candidate and another rear end position candidate into account, the process proceeds to step S511. In step S511, it is judged whether or not the other operation area (cross-sectional image operation area 431, image reproduction operation area 433) has been operated.

In step S511, when it is judged that the other operation area has not been operated, the process returns to step S510. On the other hand, in step S511, when it is judged that the other operation area has been operated, the process proceeds to step S512, the cross-sectional image display area 610 is returned to one picture screen and the display process at the time of operating the longitudinal-sectional image is terminated.

As is clear from the explanation above, in the imaging apparatus for diagnosis relating to this embodiment disclosed by way of example, by pushing down the length measurement button 601, the cross-sectional image display area is divided into two areas, and the cross-sectional images corresponding to the positions indicated by the distal end position indicator and the rear end position indicator are displayed on the respective rectangular areas and concurrently, after the positions of the distal end position indicator and the rear end position indicator are determined, the distance between the two indicators is calculated and displayed on the cross-sectional image display area.

Thus, it become possible for a user to visually confirm the cross-sectional images of the distal end position candidate and the rear end position candidate of the stent simultaneously in case of indwelling the stent and concurrently, it becomes possible to identify the distance between the distal end position candidate and the rear end position candidate.

As a result thereof, it becomes possible to relatively easily select and determine the position and the length of the stent to be indwelled. This embodiment disclosed by way of example is constructed so that the length measurement button 601 can be pushed down twice continuously, but the disclosure here is not limited in this regard. It is also possible for the number of times by which the length measurement button 601 can be pushed down to be one or three or more. Also, the shape of the divided cross-sectional image display area is rectangular, but is not limited in this regard as it is also possible that the shape of the divided cross-sectional image display area can be a triangle, a trapezoid, a circle or the like.

Second Embodiment

The first embodiment of the imaging apparatus for diagnosis and the display method described above by way of example is constructed so that the length measurement button 601 can be pushed down plural times so as to take into account the position and the length of the stent to be indwelled. However, the disclosure is not limited by this aspect and, for example, under a situation in which the length of the stent to be indwelled is limited beforehand, it is enough if only the position of the stent to be indwelled is taken into account. Consequently, in the imaging apparatus for diagnosis relating to this embodiment, in such a case, an arrangement is provided to facilitate the user's operation. Hereinafter, it will be explained with respect to a constitution of the imaging apparatus for diagnosis relating to this embodiment disclosed as a another example of the image diagnostic apparatus and display method disclosed here.

Figure 10:
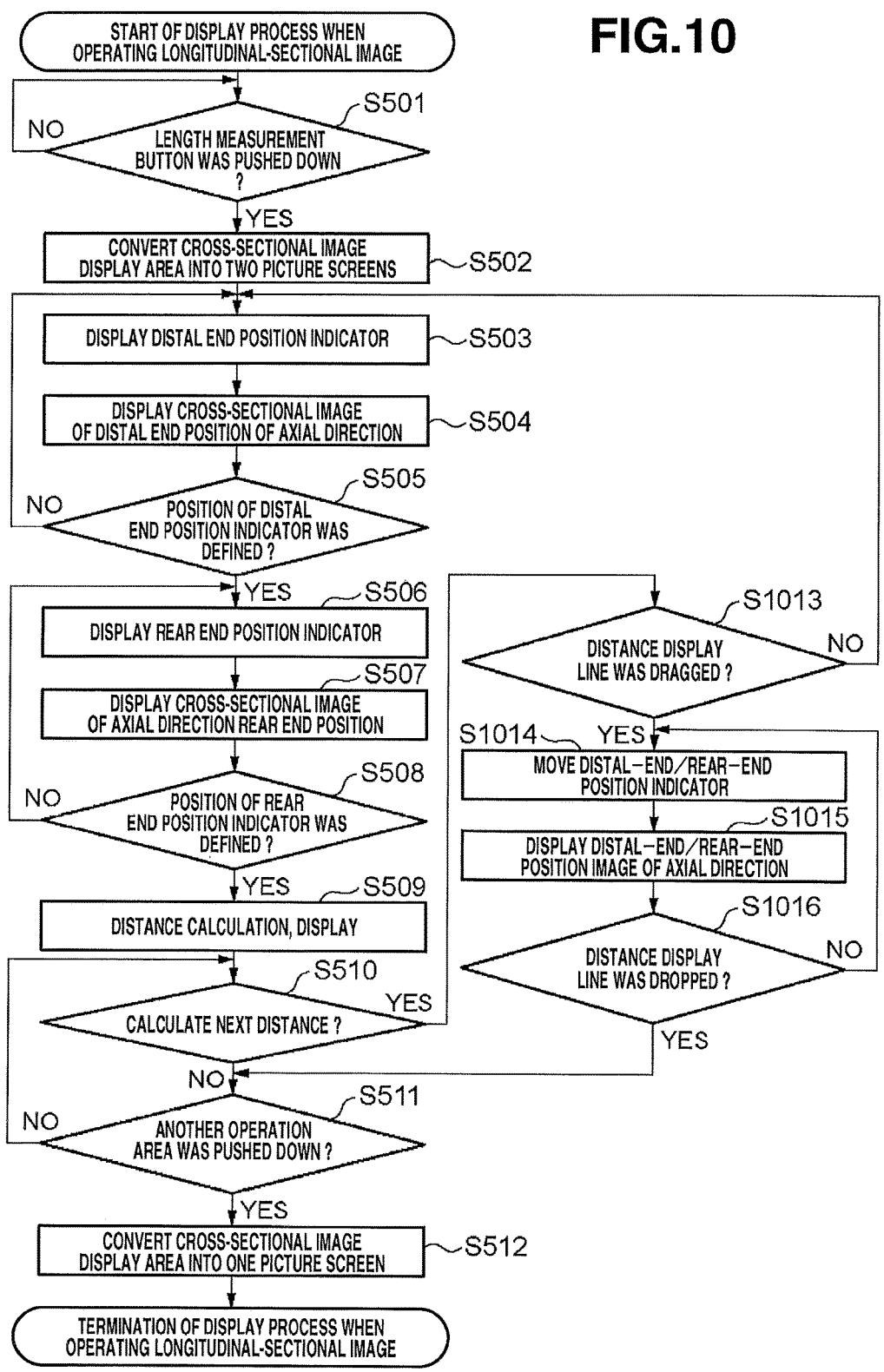
FIG. 10 is a flowchart showing a flow of a display process when operating a longitudinal-sectional image.

FIG. 10 is a flowchart showing a flow of a display process or routine when operating the longitudinal-sectional image in the imaging apparatus for diagnosis relating to this second embodiment. The processes from step S501 to step S510 are the same as the processes which are explained with reference to FIG. 5 in the first embodiment described above and illustrated in the drawing figures, so that the explanation thereof will not be repeated.

In step S1013, it is judged whether or not the distance display line is dragged by the mouse pointer. The distance display line is an arrow symbol displayed between the distal end position indicator and the rear end position indicator at the time when the positions of the distal end position indicator and the rear end position indicator are determined and the calculated distance between both the indicators is displayed on the longitudinal-sectional image display area 420.

In step S1013, in a case in which the distance display line is not dragged, the process waits until a predetermined time period elapses, and in a case in which it is judged that the distance display line is not dragged even if the predetermined time period elapsed, the process returns to step S503. On the other hand, in step S1013, in a case in which it is judged that the distance display line has been dragged, the process proceeds to step S1014.

In step S1014, the distal end position indicator and the rear end position indicator are moved together with the distance display line while maintaining the distance shown by the distance display line.

In step S1015, the cross-sectional images corresponding to the respective positions of the distal end position indicator and the rear end position indicator, which are moved by dragging the distance display line, are displayed on the rectangular areas 611, 612.

FIG. 11 is a diagram showing an aspect in which the distance display line is dragged and moved in the right direction (in the plane of the paper) within the longitudinal-sectional image display area 420. As shown in FIG. 11, the distal end position indicator and the rear end position indicator are moved in parallel while maintaining the distance shown by the distance display line.

By adding such a function, for example, by setting the distance between the distal end position indicator and the rear end position indicator to be the predetermined length of the stent, it becomes possible for a user to visually confirm the cross-sectional image corresponding to the position indicated by the distal end position indicator and the cross-sectional image corresponding to the position indicated by the rear end position indicator simultaneously while maintaining the length.

As a result, it becomes possible for a user to relatively easily select and determine the position of the stent to be indwelled in a case in which the length of the stent is determined.

Third Embodiment

The first and second embodiments of the image diagnostic apparatus and the image display method disclosed above by way of examples are constructed such that the positions of the distal end position indicator and the rear end position indicator are indicated separately and determined respectively. Bu the disclosure is not limited in this regard, and in a case in which the length of the stent is predetermined, it is possible to be constituted or constructed so that the length (length of the stent) is inputted beforehand and when the position of the distal end position indicator is designated or determined, the position of the rear end position indicator is determined and displayed automatically. Alternatively, it is possible to construct the apparatus and method such that the rear end position indicator is displayed by inputting the stent length after designating or determining the distal end position.

Fourth Embodiment

In the first to third embodiments of the image diagnostic apparatus and the image display method disclosed above by way of example, the indicators in the longitudinal-sectional images are made to have a constitution in which the distal end position indicator and the rear end position indicator are displayed; further, there is allowed such a constitution as to display the third indicator at the central position or another arbitrary position. In this case, in order to display the cross-sectional images at the positions corresponding to the three indicators, the second display area is divided into three rectangular areas. Thus, it is possible to confirm the cross-sectional images not only in the distal end position and the rear end position but also in the intermediate position of the stent.

Fifth Embodiment

In the first to fourth embodiments of the image diagnostic apparatus and the image display method disclosed above by way of example, although not particularly discussed, the color of the distal end position indicator and the color of the outer peripheral portion of the rectangular area on which there is displayed the cross-sectional image corresponding to the position indicated by the distal end position indicator can be constituted identically (i.e., may be the same color). Similarly, the color of the rear end position indicator and the color of the outer peripheral portion of the rectangular area on which there is displayed the cross-sectional image corresponding to the position indicated by the rear end position indicator can be constituted identically (i.e., may be the same color). It thus becomes possible for a user to grasp relatively easily which cross-sectional images corresponding to the positions indicated by any of the indicators the cross-sectional images displayed on the rectangular areas 611, 612 are.

Also, in the first to fifth embodiments disclosed above by way of example, the image diagnostic apparatus and the image display method are explained using as an example an optical frequency domain imaging (OFDI) apparatus utilizing wavelength sweep. But the present invention is not limited in this regard and, for example, it is possible to be applied to an optical coherent tomography (OCT) apparatus. Also, it is possible to be applied to an ultrasound imaging apparatus for diagnosis, which obtains cross-sectional images of a body lumen by an ultrasound probe including an ultrasound transducer at the distal end thereof.

The detailed description above describes features and aspects of embodiments of an imaging apparatus for diagnosis and a display method disclosed by way of example. The invention is not limited, however, to the precise embodiments and variations described. Changes, modifications and equivalents can be employed by one skilled in the art without departing from the spirit and scope of the invention as defined in the appended claims. It is expressly intended that all such changes, modifications and equivalents which fall within the scope of the claims are embraced by the claims.

What is claimed is:

1. An imaging apparatus for diagnosis comprising:
   a probe configured to be inserted within a living body lumen and comprising an imaging core configured to carry out signal transmission and reception while moving continuously in an axial direction in the living body lumen and to obtain signals reflected from tissue of the living body lumen;
   a signal processing unit configured to construct a plurality of living body lumen cross-sectional images in a direction perpendicular to the axial direction of the living body lumen based on the reflected signal; and
   a display unit comprising a first display area configured to display a longitudinal living body lumen cross-sectional image in an axial direction of the living body lumen constructed using data which is used to construct the respective living body lumen cross-sectional images, and a second display area configured to display the living body lumen cross-sectional image corresponding to an arbitrary position in an axial direction in the longitudinal-sectional image displayed in the first display area;
   wherein the signal processing unit is configured to divide the second display area into at least two individual areas when accepting an instruction that a predetermined operation is executed with respect to the first display area, and display at least two indicators for indicating the position of the axial direction in the longitudinal-sectional image in the first display area in case of accepting the instruction that the predetermined operation is executed;
   the display unit simultaneously displays a plurality of perpendicular living body lumen cross-sectional images in the direction perpendicular to the axial direction of the living body lumen corresponding to the axial direction position indicated by at least two indicators, in respective individual areas of the second display area, in a case in which the second display area is divided into at least two individual areas;
   in a case in which the positions indicated by two indicators within the indicators are determined, the distance between the two indicators is calculated, and the calculated distance is displayed in the first display area;
   when displaying the calculated distance in the first display area, a distance display line connecting the two indicators is displayed between the two indicators; and
   in a case in which the distance display line is dragged after the distance between the two indicators is calculated and the calculated distance is displayed in the first display area, the two indicators are movable in parallel in the axial direction while maintaining a fixed distance in the axial direction between the two indicators, and the perpendicular living body lumen cross-sectional images displayed in the second display area are changed in conjunction with moves of the two indicators.

2. The imaging apparatus for diagnosis according to claim 1, wherein in a case in which there is again accepted an instruction that a predetermined operation is executed for the first display area after the distance between the two indicators is calculated and the calculated distance is displayed in the first display area, the two indicators are deleted and another indicator is newly displayed while a situation remains in which the distance display line displayed in the first display area remains displayed.

3. The imaging apparatus for diagnosis according to claim 1, wherein while the two indicators move in parallel in the axial direction, there are displayed, in the two individual areas, living body lumen cross-sectional images respectively corresponding to the axial-direction positions indicated by the two indicators.

4. The imaging apparatus for diagnosis according to claim 1, wherein one of the indicators is colored a color that is the same as a color of the outer peripheral portion of the individual area corresponding to the one indicator, and the other indicator is colored a color that is the same as a color of the outer peripheral portion of the individual area corresponding to the other indicator.

5. An imaging apparatus for diagnosis comprising:
   a probe configured to be inserted within a living body lumen and comprising an imaging core configured to carry out signal transmission, in which signals are transmitted toward tissue in the living body lumen, and reflected signal reception, in which signals reflected from the tissue in the living body lumen are received, while moving continuously in an axial direction in the living body lumen;

a signal processing unit operatively connected to the probe and configured to use the reflected signals to generate living body lumen cross-sectional images of the tissue in a direction perpendicular to the axial direction of the living body lumen; and a display unit comprising:
- a first display area configured to display a longitudinal living body lumen cross-sectional image of the tissue in the living body lumen which has been constructed using data used to generate the living body lumen cross-sectional images, and to display a first end position indicator on the longitudinal living body lumen cross-sectional image and a second end position indicator on the longitudinal living body lumen cross-sectional image that is spaced from the first end position indicator in an axial-direction of the longitudinal living body lumen cross-sectional image; and
- a second display area different from the first display area to display a perpendicular living body lumen cross-sectional image in the direction perpendicular to the axial direction of the living body lumen of the tissue at an axial direction position of the longitudinal living body lumen cross-sectional image; and the signal processing unit being configured to divide the second display area into at least two different individual areas, including one individual area configured to display the perpendicular living body lumen cross-sectional image of the tissue at the axial-direction position of the longitudinal living body lumen cross-sectional image identified by the first end position indicator and an other individual area configured to simultaneously display the perpendicular living body lumen cross-sectional image of the tissue at the axial-direction position of the longitudinal living body lumen cross-sectional image identified by the second end position indicator;

wherein the second end position indicator is determined and displayed automatically at a position spaced a predetermined length in the axial direction from the first end position indicator, and the second display area displays two perpendicular living body lumen cross-sectional images corresponding to the first end position indicator and the second end position indicator, and the perpendicular living body lumen cross-sectional images are changed in conjunction with moves of the first end position indicator and the second end position indicator.

6. The imaging apparatus for diagnosis according to claim 5, wherein the signal processing unit calculates a distance between the first and second end position indicators, and displays the calculated distance in the first display area.

7. The imaging apparatus for diagnosis according to claim 5, wherein the signal processing unit displays, in the first display area, a distance display line extending between the first and second end position indicators.

8. The imaging apparatus for diagnosis according to claim 7, wherein a distance between the first and second end position indicators is fixed, the distance display line in the first area being movable to move both the first and second end position indicators in unison to new positions, and the signal processing unit displaying in the one and the other individual areas of the second display area the respective perpendicular living body lumen cross-sectional images of the tissue at the new positions.

9. The imaging apparatus for diagnosis according to claim 5, wherein the first end position indicator and an outer peripheral portion of the one individual area displaying the perpendicular living body lumen cross-sectional image of the tissue at the first end position indicator are colored as the same first color, and wherein the second end position indicator and an outer peripheral portion of the other individual area displaying the perpendicular living body lumen cross-sectional image of the tissue at the second end position indicator are colored as the same second color, the first and second colors being different from one another.

10. A display method in an imaging apparatus for diagnosis in which a probe inserted within a living body lumen and comprising an imaging core carrying out signal transmission and reception is moved continuously in an axial direction inside the living body lumen and reflected signals are obtained from tissue in the living body lumen, and a plurality of living body lumen cross-sectional images in a direction perpendicular to the axial direction of the living body lumen are constructed using the reflected signals, the display method comprising:

constructing a longitudinal-sectional image in an axial direction of the living body lumen, using data used for constructing the respective living body lumen cross-sectional images, and displaying the longitudinal-sectional image in a first display area;

displaying, in a second display area different from the first display area, a perpendicular living body lumen cross-sectional image in the direction perpendicular to the axial direction of the living body lumen corresponding to an arbitrary position in an axial direction in the longitudinal-sectional image displayed in the first display area;

dividing the second display area into two respective individual areas upon accepting an instruction to execute a predetermined operation with respect to the first display area;

displaying, in the first display area, at least two indicators indicating different positions in the axial-direction of the longitudinal-sectional image when accepting the instruction to execute the predetermined operation;

simultaneously displaying, in the respective individual areas of the second display, the perpendicular living body lumen cross-sectional images corresponding to the axial-direction positions of the at least two indicators;

displaying, in the first display area, a distance display line extending between the two indicators; and moving the distance display line in the axial direction while maintaining a fixed distance in the axial direction between the two indicators to move each of the two indicators to respective new positions on the longitudinal-sectional image, and displaying in the respective individual areas of the second display the perpendicular living body lumen cross-sectional images of the tissue at the respective new positions such that the displayed perpendicular living body lumen cross-sectional images change in conjunction with moves of the two indicators.

11. The display method according to claim 10, wherein the predetermined operation with respect to the first display area comprises operating a length measurement button to individually set the two indicators.

12. The display method according to claim 10, further comprising calculating a distance between the two indicators, and displaying the calculated distance in the first display area.

13. The display method according to claim 10, further comprising moving at least one of the two indicators to a respective new position on the longitudinal-sectional image, and displaying in the respective individual area of the second display the perpendicular living body lumen cross-sectional image of the tissue at the new position.

14. The display method according to claim 10, further comprising coloring one of the two indicators and an outer peripheral portion of the individual area of the second display area displaying the perpendicular living body lumen cross-sectional image of the tissue at the one indicator a common first color, and coloring the other of the two indicators and an outer peripheral portion of the individual area of the second display area displaying the perpendicular living body lumen cross-sectional image of the tissue at the other indicator a common second color that is different from the first color.

* * * * *